(12) United States Patent
Routburg et al.

(10) Patent No.: US 6,981,640 B2
(45) Date of Patent: Jan. 3, 2006

(54) METHOD AND SYSTEM FOR ASSISTED CULLING AND REFORMATTING OF ENCODED MICROTUBES

(75) Inventors: Michael Stanley Routburg, West Hartford, CT (US); Kenneth Hendrata, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 187 days.

(21) Appl. No.: 10/650,902

(22) Filed: Aug. 27, 2003

(65) Prior Publication Data

US 2005/0049799 A1 Mar. 3, 2005

(51) Int. Cl.
*G06F 17/60* (2006.01)
(52) U.S. Cl. .......................... 235/382; 702/19; 422/63; 136/47
(58) Field of Classification Search ................ 235/385, 235/435, 439, 454, 462.01; 702/19, 22, 31; 422/63, 64–65, 67, 68.1, 100, 104; 436/47, 436/43, 48
See application file for complete search history.

(56) References Cited

U.S. PATENT DOCUMENTS

| | | | | |
|---|---|---|---|---|
| 4,701,754 A | * | 10/1987 | Provonchee | 340/815.45 |
| 5,096,670 A | * | 3/1992 | Harris et al. | 422/65 |
| 5,316,726 A | * | 5/1994 | Babson et al. | 422/65 |
| 6,500,609 B1 | * | 12/2002 | Ribeill et al. | 435/4 |
| 2002/0064881 A1 | * | 5/2002 | Devlin et al. | 436/43 |
| 2005/0013736 A1 | * | 1/2005 | McKeever | 422/63 |

OTHER PUBLICATIONS

U.S. Appl. No. 60/488,689, filed Jul. 18, 2003, McKeever.*

* cited by examiner

*Primary Examiner*—Diane I. Lee

(74) *Attorney, Agent, or Firm*—Michael P. Morris; Mary-Ellen M. Devlin; Alan R. Stempel

(57) ABSTRACT

A method and system for aiding the selecting/culling or reformatting of encoded containers stored in a multi-rack array with respect to certain desired characteristics of compositions held within the containers employing a corresponding graphical interface that indicates the physical position of the containers within the array, and selection operations to be performed with respect to one or more containers in the array.

17 Claims, 15 Drawing Sheets

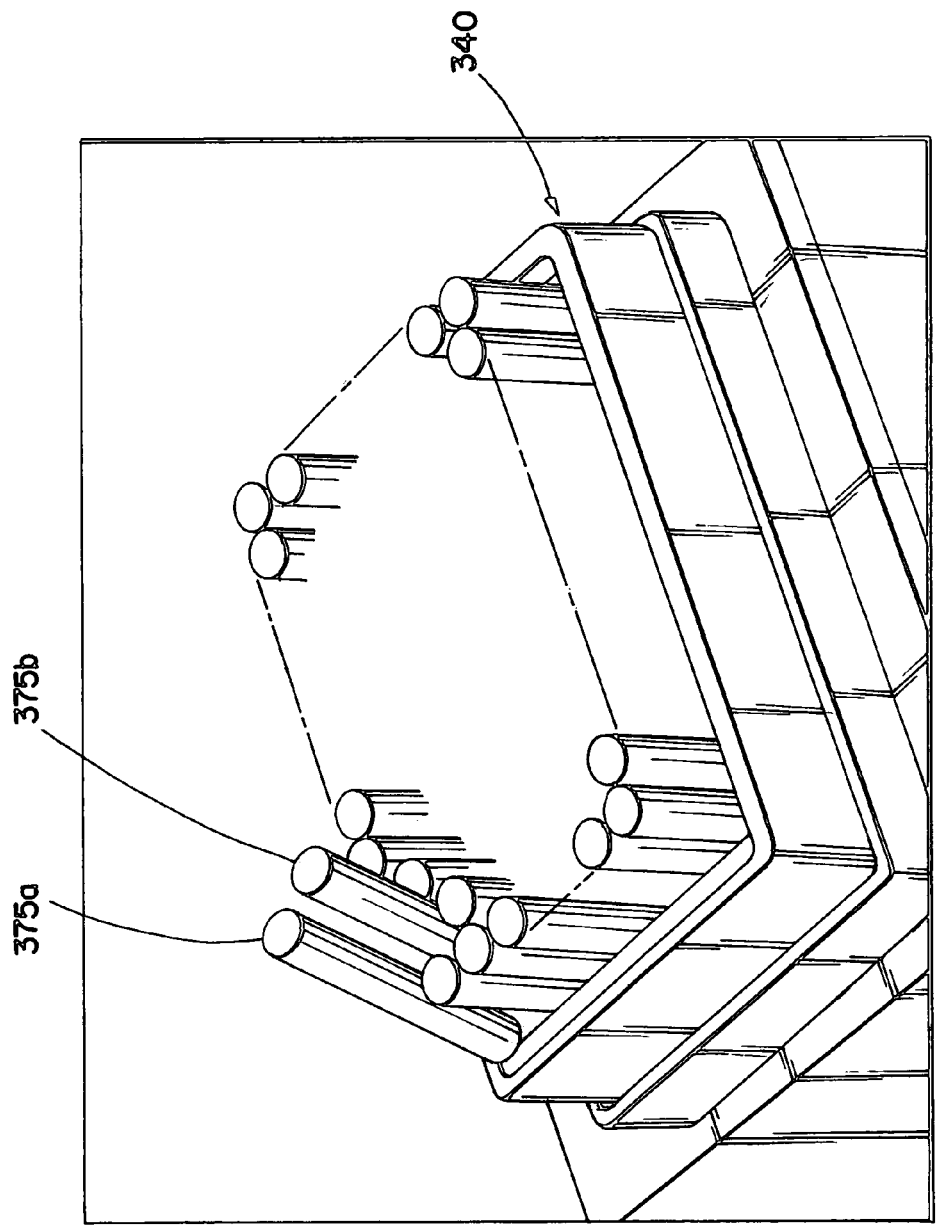

METHOD AND SYSTEM FOR ASSISTED CULLING AND REFORMATTING OF ENCODED MICROTUBES

BACKGROUND

1. Field of Invention

The present invention generally relates to a method and system for the easy identification and culling of one or more of a plurality of encoded objects that are each associated with an individual retention position on a holding means or a rack, and for re-association of each encoded object with a new retention position if such encoded object is moved. More specifically, the present invention describes in one embodiment a method and a system which assists in the culling of encoded objects on the entire rack of encoded objects using a scan-readable symbology which is continuously updated (in real time). The method and system of the present invention presents a graphical interface representative of the position of each encoded object in a multi-well rack, and of information pertaining to properties of the materials stored within such object.

2. Discussion of Related Art

Research in the biological and chemical fields has dramatically changed in a short few years from predominantly manually-based assay methodologies and synthesis protocols to nearly fully-automated assays and protocols. The automation of biological and chemical processes has led to significantly more samples which need to be tested and probed.

Examples of automated processes which have greatly increased the number of samples which require analysis are combinatorial chemistry and parallel synthesis. Such methods are powerful techniques for increasing a chemist's productivity. It allows the chemist to produce large libraries of compounds relatively quickly. Prior to the advent of combinatorial chemistry and parallel synthesis, the process to discover new drugs had not changed significantly for over 100 years. Combinatorial chemistry and parallel synthesis changed forever the dogma that chemical entities should be synthesized, purified and analyzed one at a time. Combinatorial chemistry generates every possible variant, while parallel synthesis generates a subset for more intensive testing. In the parlance of the art, the phrase "combinatorial library" is often used to refer to a library of compounds generated to find and/or generate lead compounds, while the phrase "lead optimization library" is used to describe a library of compounds built around a previously identified lead compound.

In conventional combinatorial synthesis, compounds are conventionally synthesized on plastic beads that are segregated into different containers. In each container a different chemical building block is added to the beads. The beads from each container are then divided among a new set of containers and new building blocks added to each container. Once a lead series of compounds is identified in a combinatorial library, parallel synthesis is often employed. Parallel synthesis provides more flexibility in generating compounds. The chemistry may be performed using solid phase or solution phase chemistry.

Three common approaches are used in combinatorial organic synthesis. The first method employs arrays wherein synthesis is spatially addressable, building blocks being systematically reacted in individual reaction wells or positions to form separated discrete molecules. Active compounds are identified by their location in the array. A second technique, known as encoded mixture synthesis, uses inert chemical tags to identify each compound. The third approach, referred to as deconvolution, prepares a series of compound mixtures with each mixture being assayed, and the most active combination pursued. Such technique is typically employed in peptide optimization.

Typically in an array system, compositions are housed in either wells or in tubes, either of which are placed in a holding system or rack to generate a plurality of wells. The difficulty with using multi-well plates is that the scale of reactions can be limited due to the size of the wells, and it may be difficult to determine chemical yield as it is difficult to obtain the weight of individual samples in a plurality of wells. The use of multi-tube configurations, i.e., tubes to be placed within the well-rack locations, improves scale up of synthesis, but suffers from the disadvantage that error may be introduced if the tubes are misplaced in their well-rack locations.

Typically in combinatorial chemistry processes, a series of compounds are synthesized in multi-tube racks or multi-well plates. The location of each individual tube or well must be stored in a database handled by a computer system to allow association of the compounds with a particular position in the rack or well plate. After synthesis, the contents of each tube or well is generally transferred to a device for purification. Purification may be, for example, by means of a chromatographic device, such as a preparative scale HPLC, GC, preparatory supercritical fluid chromatography, or column chromatography. Various means are known in the art to identify compounds of interest when eluting from a column, including GC-MS, FID, NMR, ELSD, TLC, IR and UV. The solvent is then typically removed from each purified fraction, as, for example, by centrifugation or by vacuum oven, and the individual tubes weighed to gain information on percent yield. Thereafter, one or more chemical analyses are conventionally performed on the purified compounds, and the compounds are transferred to one or more multi-well plates or multi-tube racks for subsequent bioassay.

Multi-tube configurations in combinatorial arrays often include 48 or 96 tubes or more. Unfortunately, owing to lack of standardization, automated purification and chemical analysis equipment is not necessarily designed around the number of tubes in the multi-tube configurations used to prepare the compounds. The latter makes it quite difficult to track the identity and properties of compounds as they progress through stages of synthesis, purification and chemical analysis. In processing of the compositions housed within a tube, it is important to be able to identify precisely the location of the tube in the array.

Numerous methods have been employed in the tracking of tubes in combinatorial arrays. Probably the oldest known entails alphanumeric labeling of each tube. The problem with alphanumeric labeling is that once the labeled tube is dissociated from its known position within a bar coded rack, its previous identification is meaningless. Future identification is totally dependent on the storage database, and flawless retrieval from the storage system by robotics. Another of these methods entails placing a bar code on each tube in a multi-tube configuration. The bar codes permit one to keep track of the tubes, in particular to tubes that are moved to and from different multi-tube racks with varying numbers of tubes per rack. For example, MDS Panlabs produces a system that synthesizes compounds at a 1 mmole scale in multi-tube configurations in which each tube in the configuration is identified with a bar code, and is moved from stages of synthesis, purification and chemical analysis (typically including flow inject mass spectrometry) by means of robotic arms after the tube is optically read. Bar codes are typically attached using an adhesive, but could also be etched or otherwise affixed to the tubes.

As the size of many combinatorial libraries is great, it has been found in the art to be a tremendous burden to place, and keep track of, individual bar-codes on a plurality of tubes.

WO 00/47500 describes one process for overcoming such problem associated with the bar-coding of individual tubes. In such system, computer software is used to record the relative position of individual tubes, and the compounds within each tube, in a computer database. Automated means, by way of robotic arms, are used for transferring tubes from one multi-tube configuration to another with the position of the tubes in the first multi-tube configuration being correlated to the position of the tubes in the second multi-tube configuration. In short, instead of labeling each tube and monitoring the movement of each tube, the system employs relational database software which correlates the orientation of the tubes as a whole between more than one multi-rack.

The problem with the solution provided by WO 00/47500 is that for operation the system requires exact fidelity in the movement of the tubes between multi-racks. That is, it does not account for errors that may occur in movement, such as broken tubes, nor does it account for the desirability in many cases for analysis, such as bioassays, of certain samples to be halted with respect to one or more tubes due to factors such as poor purity or low sample size (e.g., the culling of samples from the whole). For example, if samples should fall from a rack during transport, there may be little to no possibility to positively identify the tube/sample without significant diagnostics. It also does not effectively deal with activities that result in the removal of tubes, such as microtubes, from the array, e.g., "cherry picking" of tubes, reformatting of tubes to compress storage, or culling of undesired tubes from a set (e.g., combichem post analytical). Further, because of the high fidelity requirement, the system employs expensive automated components that greatly increase the cost and complexity of the combinatorial chemistry analysis.

There is therefore the need for a simpler and cheaper system for assuring the identification of samples across processing, which allows for rapid visual verification of complete accuracy.

SUMMARY OF INVENTION

The present invention overcomes the disadvantages of the prior art in continuously monitoring the position of encoded tubes in holding systems, such as racks that can hold numerous tubes, i.e., a multi-rack, and in providing a graphical interface that indicates the position of each encoded tube and graphically indicates with respect to one or more encoded tubes properties associated with the compounds housed within such encoded tubes. Such method makes use of individual identification means affixed to each tube to provide the security that the actual compound in the tube is identified when the samples move from the combinatorial chemistry laboratory to the dispensary.

By "tube" it is meant any suitable container that can contain from about 1 mg to about 1 gram of a compound. By "encoded tube" it is meant a tube which has associated therewith, in or on, a unique identifying symbol, code, transmission, or composition which is readable by electronic means, but does not include a tube that is identified simply by alphanumeric characters. An encoded tube may therefore have associated with it a symbology, such as a bar code, an ASIC, a transponder, a particular fluorescent compound in a particular concentration, etc. By "scanner" or "reader" it is meant any device for optically or electronically detecting and/or deciphering the encodation associated with an encoded tube. A scanner thus includes an optical scanner, a transponder receiver, a bar code reader, etc. By "continuous scanner" it is meant a scanner that is automatically programmed or set to scan across the totality of objects described in a repetitive fashion.

The symbology associated with the tube may be a one-dimensional bar code, generally comprising a series of lines of different widths, a stacked bar code or multi-row code comprising a series of one dimensional bar codes, a two-dimensional bar code (e.g. 2D), array tag, aztec code, small aztec code, codablock, code 1, code 16K, code 49, CP code, dataglyphs, data matrix, CI matrix, dot code A, huecode, intacta.code, maxicode, minicode, PDF 417, micro PDF 417, QR code, smartcode, snowflake code, supercode, or ultracode that codes the data based on the spots within a matrix and codes information along the height as well as the length of the symbol, or a three-dimensional bar codes, a code that is read by using differences in height, rather than contrast, to distinguish between bars and spaces using a special reader. A preferred symbology is data matrix which is a dense code which contains sufficient redundancy within the structure to allow some of the code to be damaged and still decode. It also has characteristics that allow the code to be read in any rotational orientation. Of course, along with such symbology, other identifying markings, such as alphanumeric numbering, may also be employed. An applied symbology should be resistant to wear and solvents that may be employed in processing. For example, a symbology may be preferred to resist 4 hours of direct contact with a 50% TFA, or a 100% DMSO solvent, or greater than 24 hours vapor contact with the same solvent mixtures.

The encoded tube is preferably associated with the compound it contains at weighing. The identification of the tube should be checked for duplication of identification numbers within a data base.

The invention provides in one embodiment a continuous scanner that reads and deciphers unique symbology incorporated on or in a tube housed within a multi-rack array, a display, both of which are coupled to a data processing unit having access to a database of information related to one or more properties of the composition retained within one ore more tubes in the multi-rack array. Such embodiment preferably includes software responsive to input from the continuous scanner to visually positionally-display the identity of each tube within the multi-rack array, and to visually display with respect to the identified tubes properties of the composition housed within one or more tubes. The identified properties may include, for example, compositions not reaching a desired level of purity. Such compositions may be marked for culling or removal so as not expend time, reagents and funds in effectuation of future procedures to be performed on the compositions within the tubes. Since the scanning is continuous, the removal of the composition to be culled will display as removed as the object is removed. The display is a one hundred percent (100%) validation that the correct composition was accessed for removal.

Image processing may make use of one or more bed scanners (generally inexpensive but slow) or more preferably digital cameras (generally faster). The optical system may enlarge the image of any symbology appended to the tube. For 96 well arrays, preferably the tubes are read and decoded within approximately 2 seconds or less. The reader may be integrated with a commercial computer/decode board interface.

BRIEF DESCRIPTION OF THE DRAWINGS

The invention claimed and/or described herein is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5(e) is a elevated view of a 96 multi-rack array of FIG. 1 wherein two tubes are being removed from the array.

DETAILED DESCRIPTION

Figure 1:
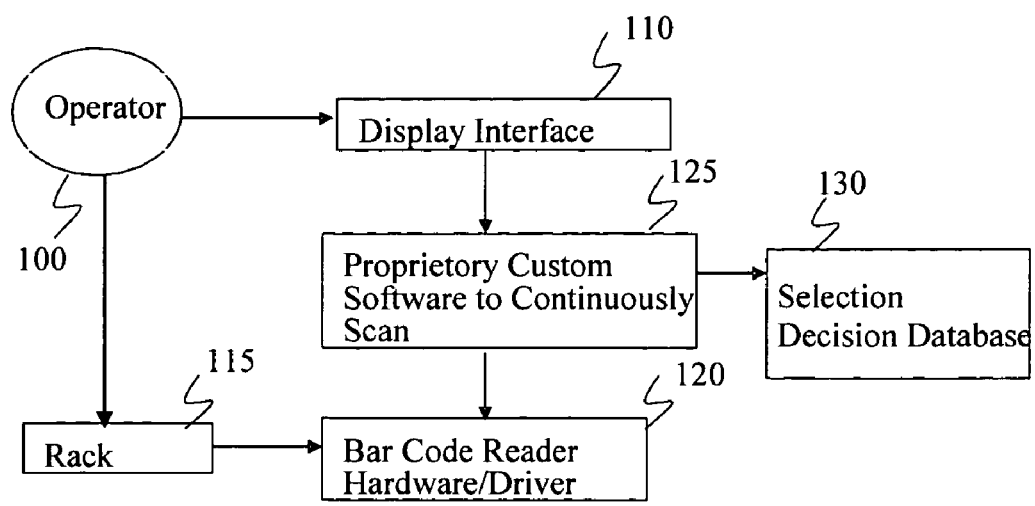
FIG. 1 is a block diagram over an embodiment of the present invention.

The present invention allows users to quickly and accurately, with real time feedback, interact with a database pertaining to properties of compositions retained in one or more tubes housed in a multi-rack array so as to be able to extract those compounds from the rack that need to be selected for further processing, testing or culling. A method and system of the present invention accomplishes such by displaying a graphical/video presentation of the rack of tubes in real time, updating the presentation automatically, and indicating visually the tubes that are to be removed. As a tube is removed from the multi-rack, the display is updated (preferably within 4 seconds or less) and visual confirmation is provided that the correct tube to be removed was selected and actually removed. That is, the display matrix matches the tube rack matrix. As a tube is removed the graphic tube disappears from the screen allowing for absolute accuracy in the manually assisted tube selection.

In one embodiment of the invention, the tubes in an array are encoded with a 2D bar code. Such bar codes are fast scanned in a continuous scan mode, to allow for graphical presentation of the rack of tubes in real time. By interfacing the bar code scanner with a data processor, such as a computer, coupled to a database storing information pertaining to the properties of one or more compositions housed within one or more tubes in the array, such as purity and weight, the display may further indicate information pertaining to which tube or tubes are to be culled or removed from the array. As the tube is removed, the display is continuously updated and visual confirmation is seen that the correct tube that was to be selected for removal was indeed removed.

The continuous scan test mode of commercially-available products such as RVSI Matrix may be used to effectuate the continuous scan of the tubes housed in the array, and adapted to provide the interactive apparatus for culling compounds described. Culling information may be inputted automatically based on measured parameters such as sample weight or purity, or may be inputted manually by the chemist.

Partial arrays may be combined with the position of each tube in the combined array being determined after scanning.

Grades of information may be graphically displayed with respect to one or more tubes in the displayed array. For example, one color might be used to indicate that the composition in a particular tube is good purity and adequate weight, another color if the composition is of good purity but not enough weight, a third color if the tube contains a composition that is of adequate weight but not of enough purity, a fourth color if the tube contains a composition that is neither pure enough nor of enough weight, a fifth color is the purity is very low or no desired compound found, and so on. Other graphical indications, such as symbols, as would be understood by one of ordinary skill in the art, could also be utilized. Information is preferably imported from a network database but may also be from a data storage device, such as a floppy disk. More simplistic representations may be employed if the decision is simply whether a tube is to be culled or not (for example, "to be culled samples" to be indicated in red, all "good samples" in green).

The culling decision may be made using a proprietary chemical software application or by the chemist.

Verification of culled tubes may be scanned individually or jointly in another rack (e.g., "culled" rack) after removal, and prior to discard.

Now turning to the figures, there is shown in FIG. 1 a block diagram overview of an embodiment of the present invention. Operator 100 initially undertakes to separate the type of compounds to be housed in a tube multi-rack 115 which contains a plurality of encoded tubes. The position of each encoded tube in the multi-rack 115 is identified by a reader 120. Output from reader 120 is fed into proprietary interface software 125, which also receives input pertaining to selection properties of compositions in one or more encoded tubes from a selection decision database 130, and which proprietary interface software 125 will provide a means to differentiate the handling of selected encoded tubes from other encoded tubes in the array. Specifically, proprietary interface software 125 outputs a graphical representation of the identity of tubes at each position of the multi-rack along with selection information onto display interface 110 for viewing by operator 100 or another.

Figure 2:
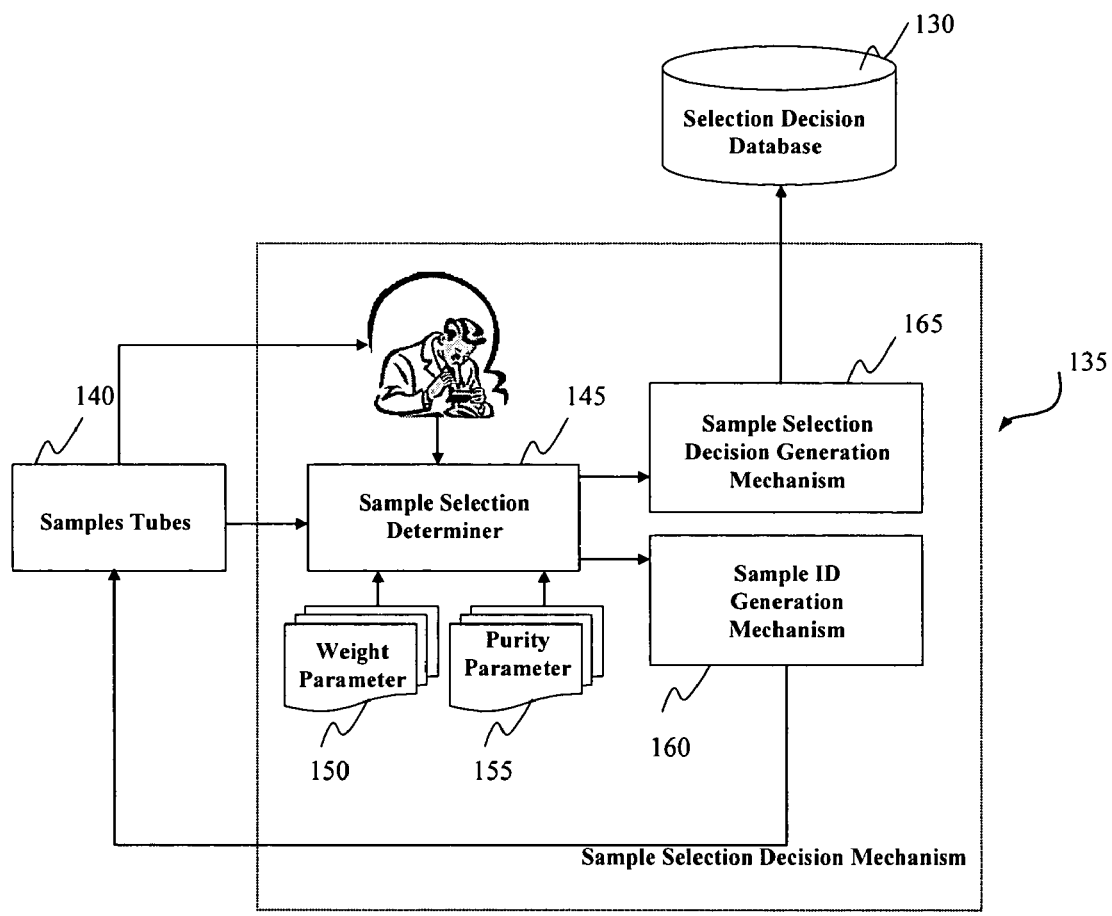
FIG. 2 is a diagram of the decisions making that may be employed with respect to generation of a selection decision database of FIG. 1.
Figure 3:
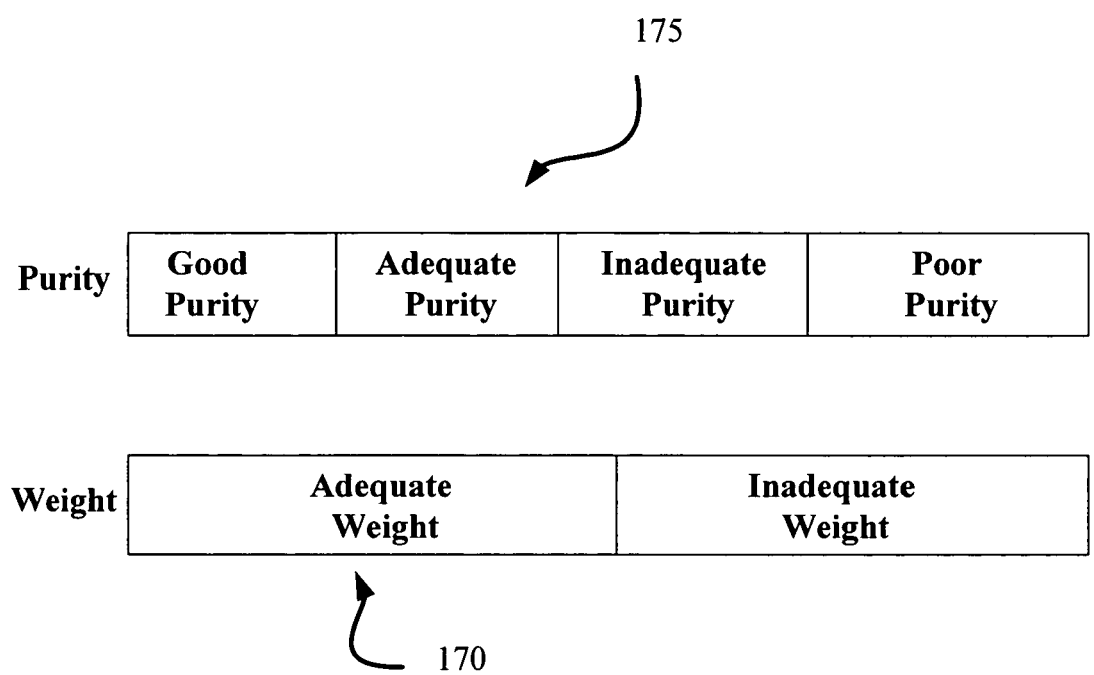
FIG. 3 is a graphical depiction of certain parameters that may be measured in the selection decision process.
Figure 4A:
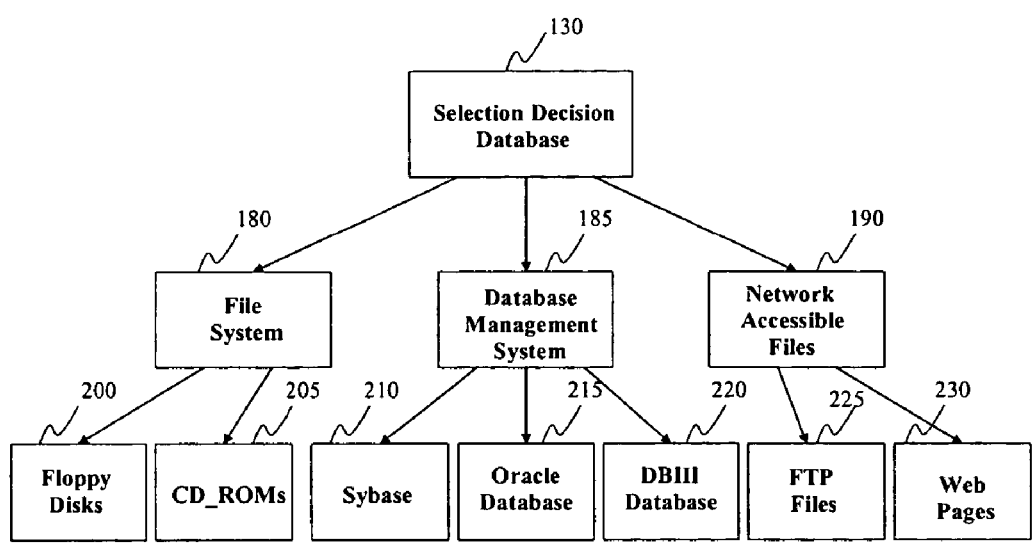
FIG. 4a is a block diagram of different storage mechanisms for storing data related to selection decisions.

FIG. 2 illustrates in diagram form the decision making which may be employed with respect to selection decision database 130. Sample selection for processing entails effectuation of a sample selection determiner 145 which may be based upon one or more parameters deemed necessary for further processing, such as a value for the composition within or meeting a certain weight parameter 150 (for example, as shown in FIG. 3 "adequate weight" or "inadequate weight" 170), or purity parameter 155 (for example, as shown in FIG. 3 "good purity," "adequate purity," "inadequate purity," or "poor purity" 175). Such sample selection determiner 145 may be used to determine whether a sample tube 140 is provided an encoding identification via sample ID generation mechanism 160 or may be used to output sample selections to sample selection decision generation mechanism 165, which inputs selection decisions into selection decision database 130. As shown in FIG. 4(a), selection decision data base 130 may comprise any storage system known to those of ordinary skill in the art including file system storage 180, database management system storage 185, or network accessible storage 190, and may include storage on or in floppy disks 200, cd-roms 205, sybase 210, oracle database 215, DBIII database 220, FTP files 225, or Web pages 230, for example.

Figure 4B:
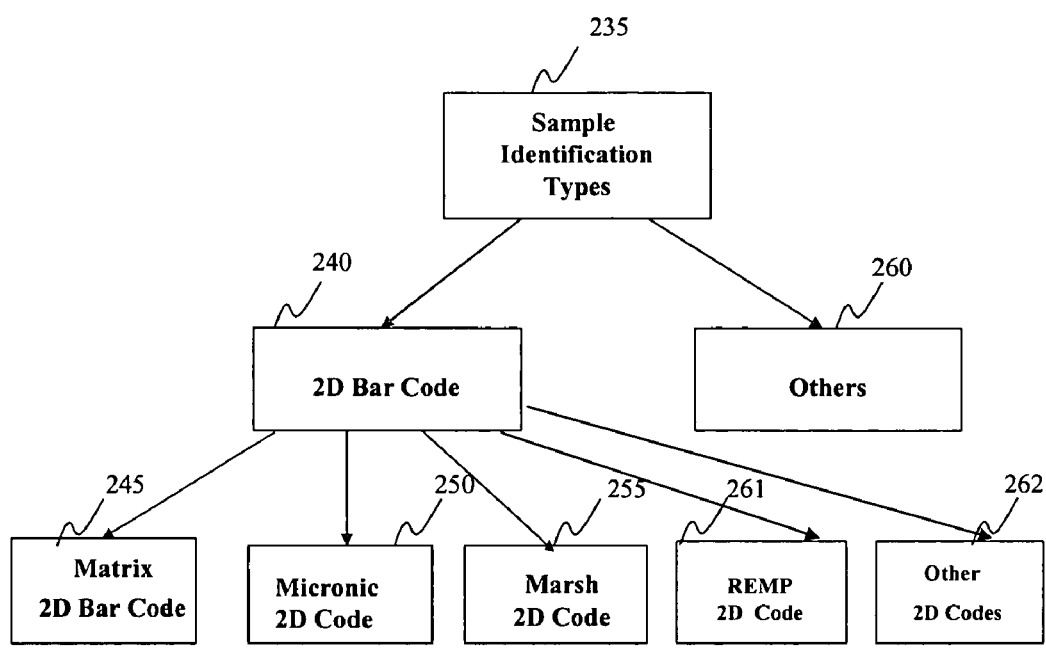
FIG. 4b is a block diagram of sample identification types.
Figure 4C:
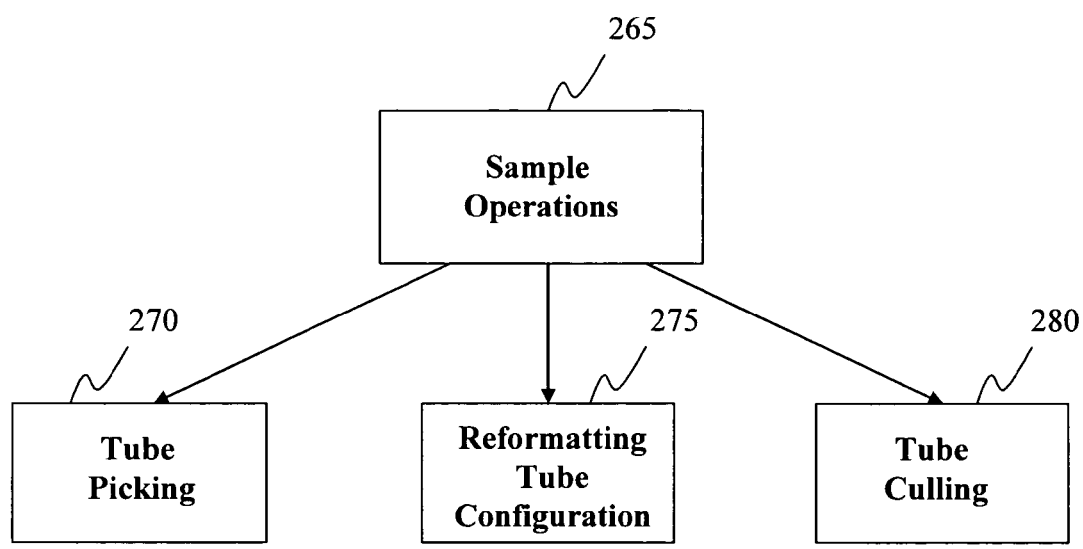
FIG. 4c is a block diagram of sample operations.

Sample ID generation mechanism 160 may encode sample tubes 140 by any number of sample identification techniques 235 as shown in FIG. 4(b), such as 2D bar code 240, which may comprise Matrix 2D bar code 245, Micronic 2D code 250, Marsh 2D code 255, or REMP 2D code 261, other 2D codes 262, or other techniques 260, such as ASIC associated with the tube. Selection of tubes from the multi-rack array may entail any number of sample operations 265, for example as shown in FIG. 4(c), including tube picking 270, reformatting of the tube configuration in the array 275, and tube culling 280.

Figure 5A:
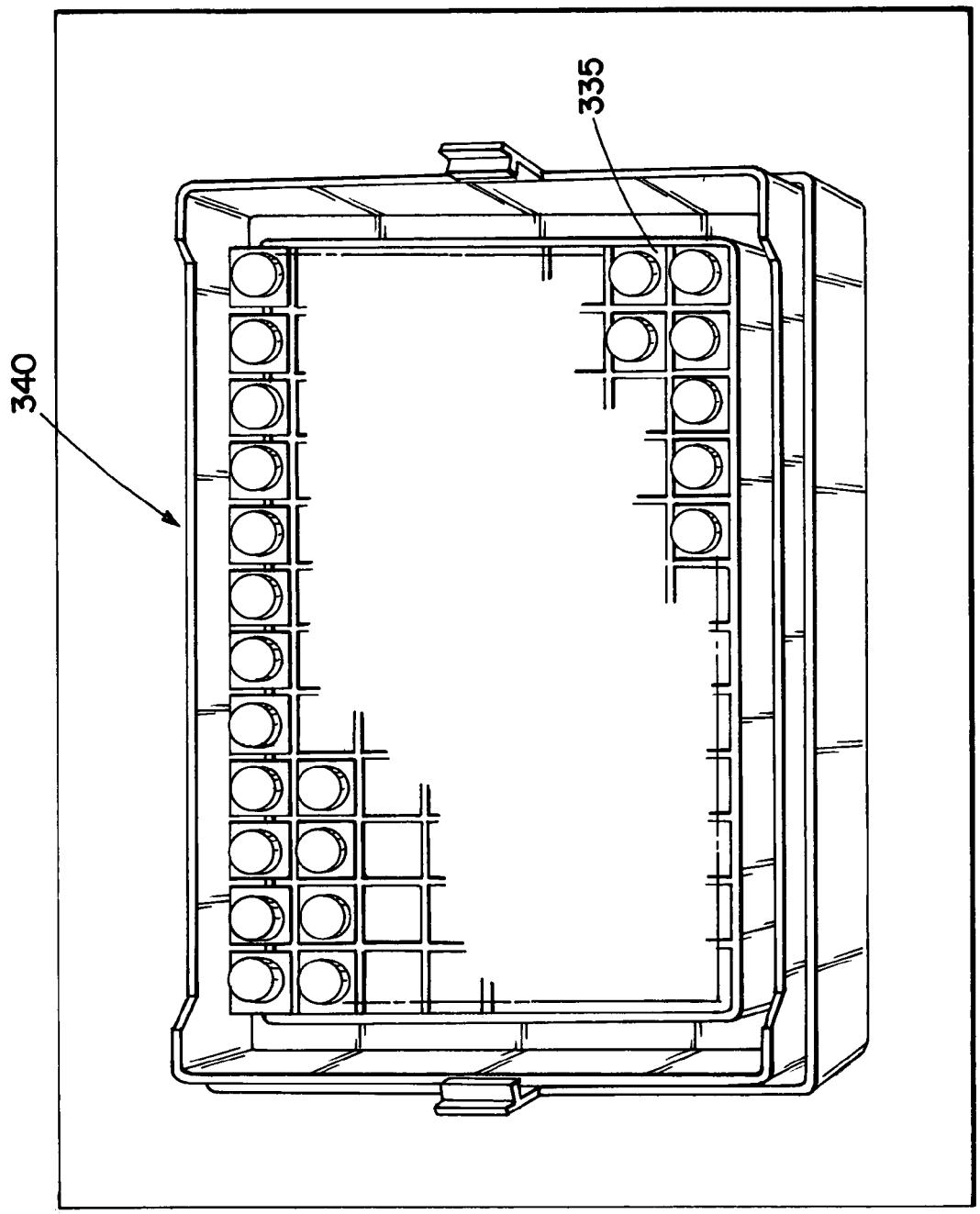
FIG. 5(a) is topical view of a 96 multi-rack array.
Figure 5B:
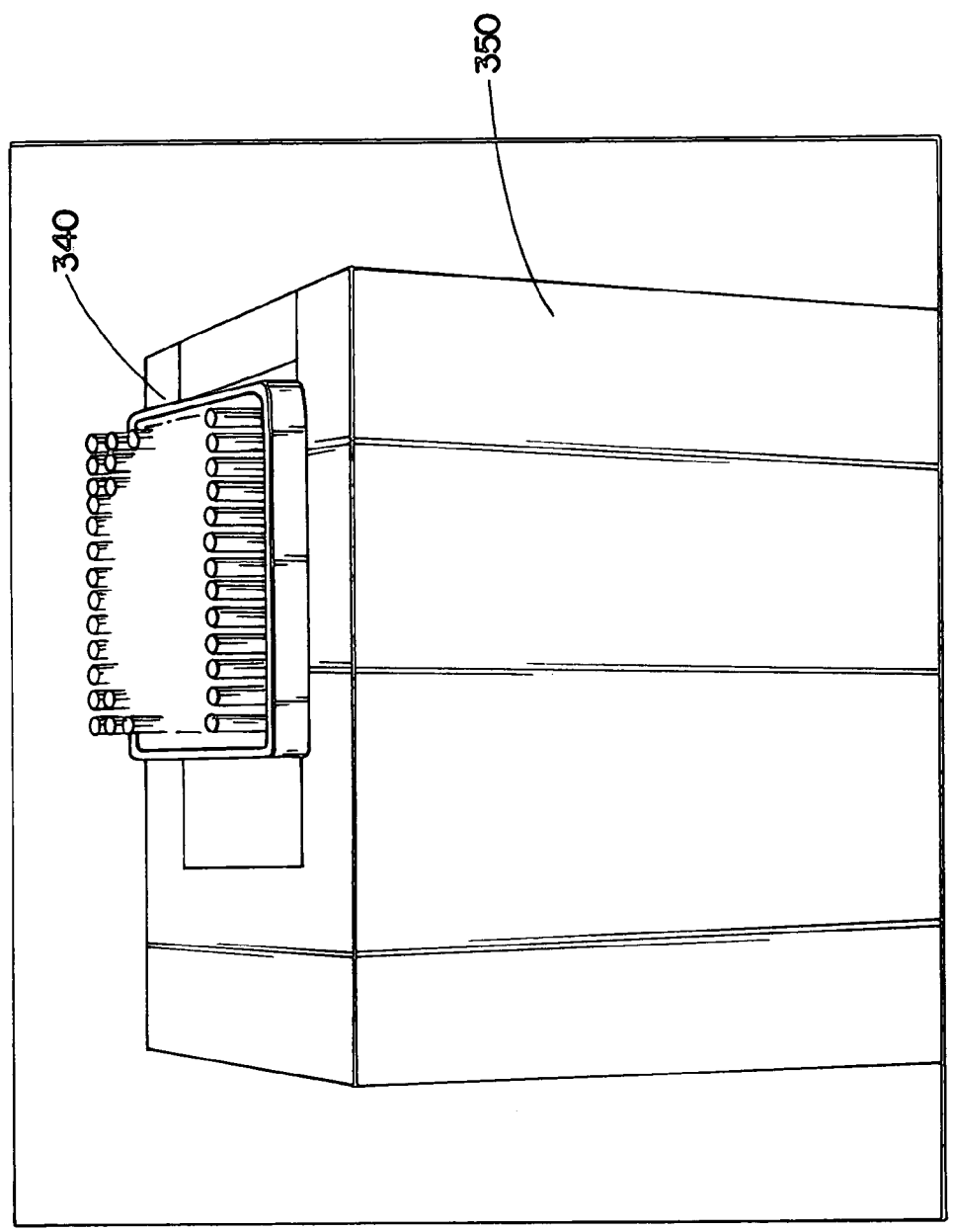
FIG. 5(b) a side perspective view of the 96 multi-rack array of FIG. 5(a) on a scanner configured to read the symbology on the bottom of each tube.
Figure 5C:
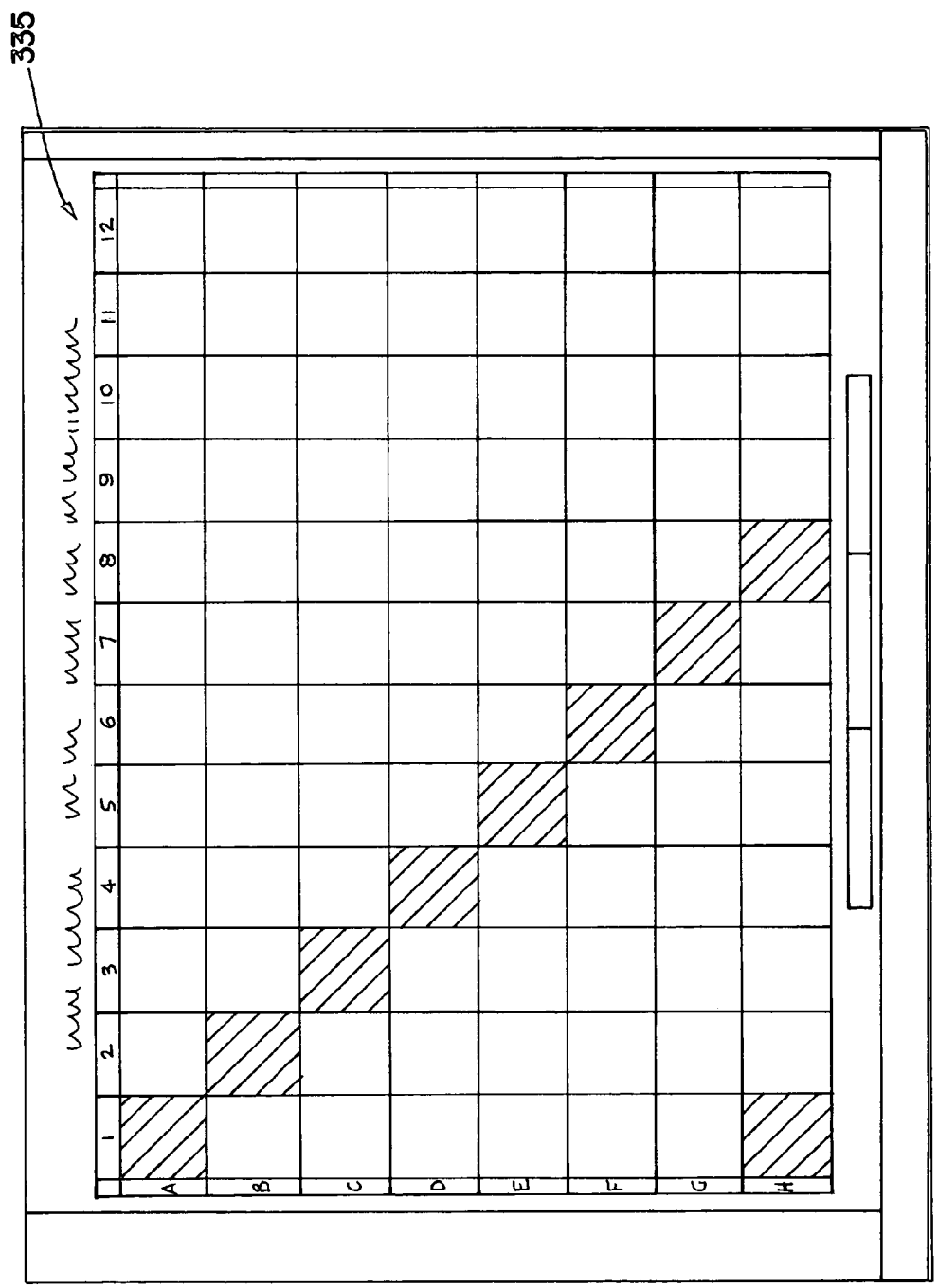
FIG. 5(c) is a face view of a graphical interface of the present invention.
Figure 5D:
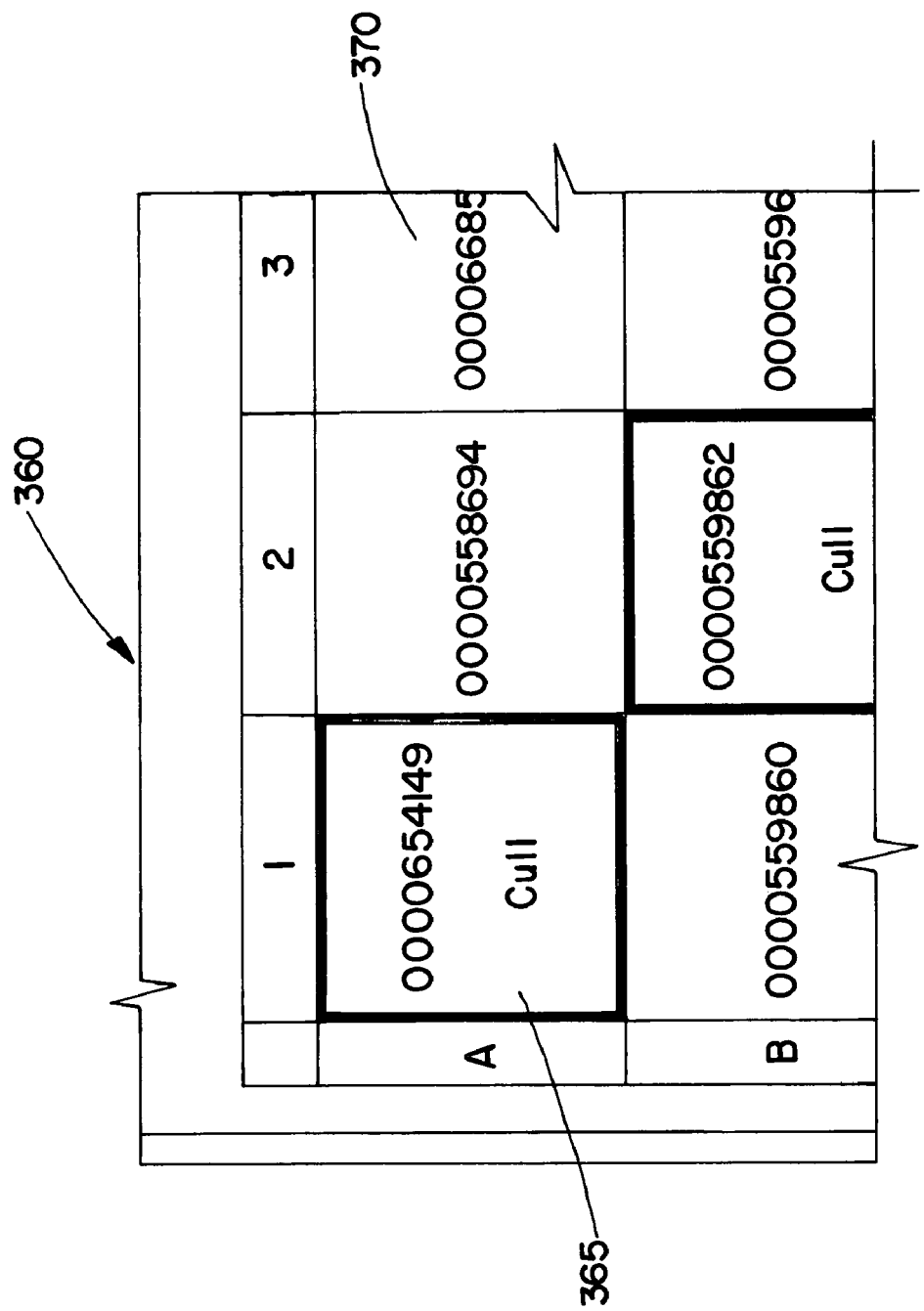
FIG. 5(d) is an exploded view of a section of the graphical interface of FIG. 5(c) illustrating the integration of the identification of tubes with selection decisions with respect to a number of such tubes shown.
Figure 5F:
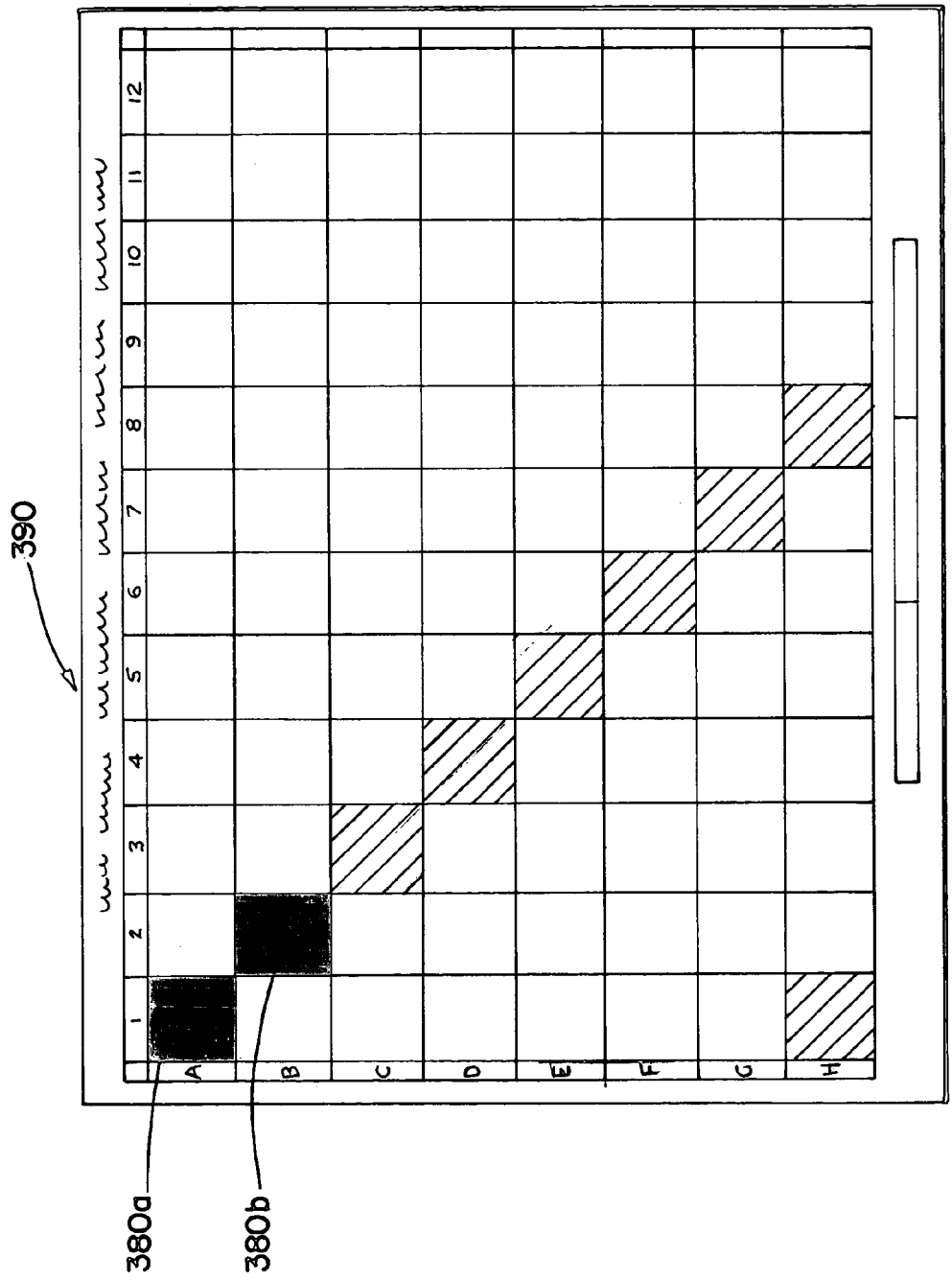
FIG. 5(f) is the graphical interface of FIG. 5(c) after removal of the two tubes shown in FIG. 5(e).

Now turning to FIG. 5(a), there is shown a topical view of a 96 multi-rack array 340. In the embodiments shown, multi-rack array 340 houses multiple encoded tubes 335 each having a 2 dimensional symbology affixed on the bottom of such encoded tubes. FIG. 5(b) a side perspective view of a 96 multi-rack array 340 of FIG. 5(a) on a scanner 350 configured to read the symbology on the bottom of each tube 335. FIG. 5(c) is a face view of a graphical interface 355 of the present invention illustrating information pertaining to the identity of the tubes integrated with information pertaining to selection operations which are desired to be performed. FIG. 5(d) shows an exploded view 360 of a section of the graphical interface of FIG. 5(c) illustrating the integration of the identification of tube identification codes 370 with selection decisions, in this case to cull the tube whose identification code is located at position A1 of the rack array 365, with respect to a number of such tubes shown. There is a one to one correlation between the physical rack and the graphical representation which allows for the user to quickly, visually confirm that the correct tube(s) has(ve) been culled.

FIG. 5(e) is an elevated view of the 96 multi-rack array 340 wherein two tubes 375a and 375b are being removed from the array. FIG. 502 is the view of the graphical interface 390 of FIG. 5(c) after removal of the two tubes shown in FIG. 5(e) with black squares 380a and 380b indicating removed tubes 375a and 375b. Again, as noted before, there is a one to one correlation between the physical rack and the graphical representation, in real time, allowing quick, visual confirmation of correct selection.

Figure 6A:
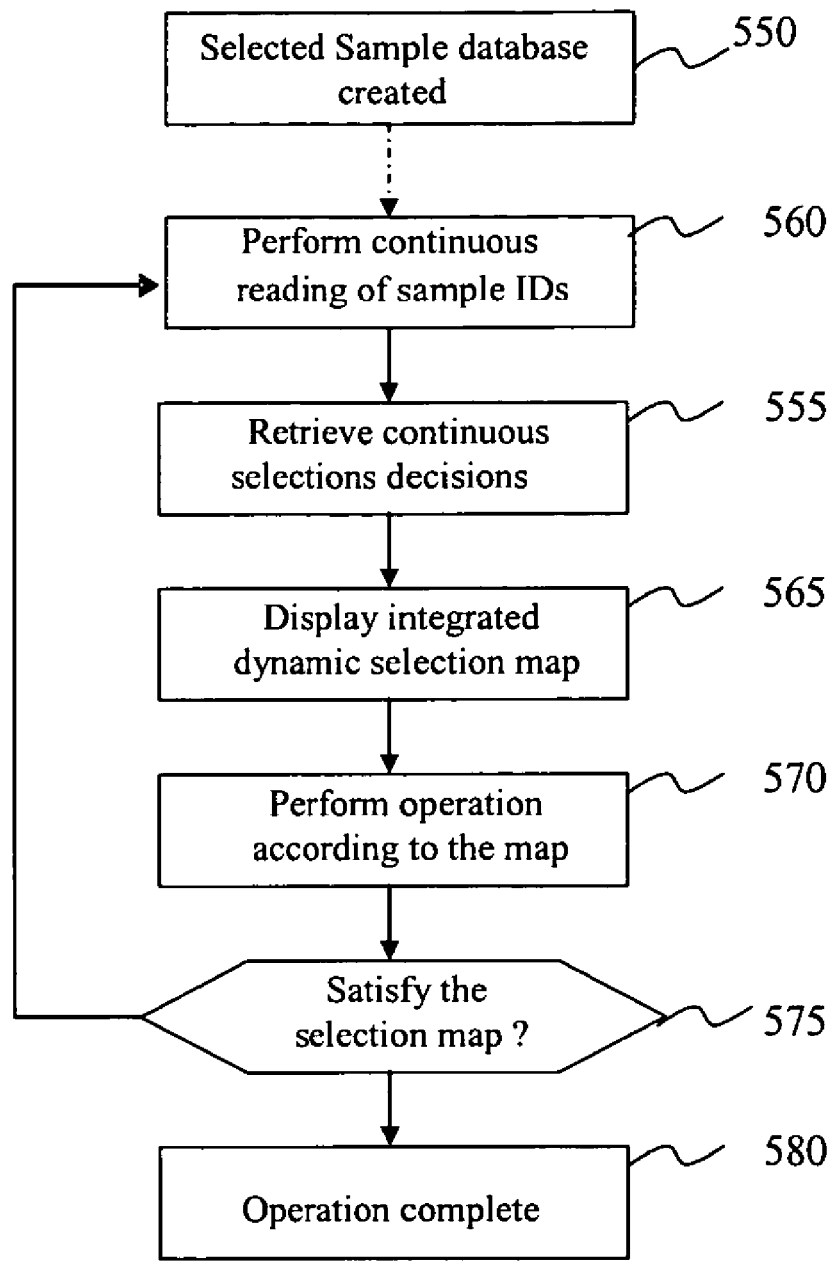
FIG. 6(a) is a block diagram of one method embodiment of the present invention.
Figure 6B:
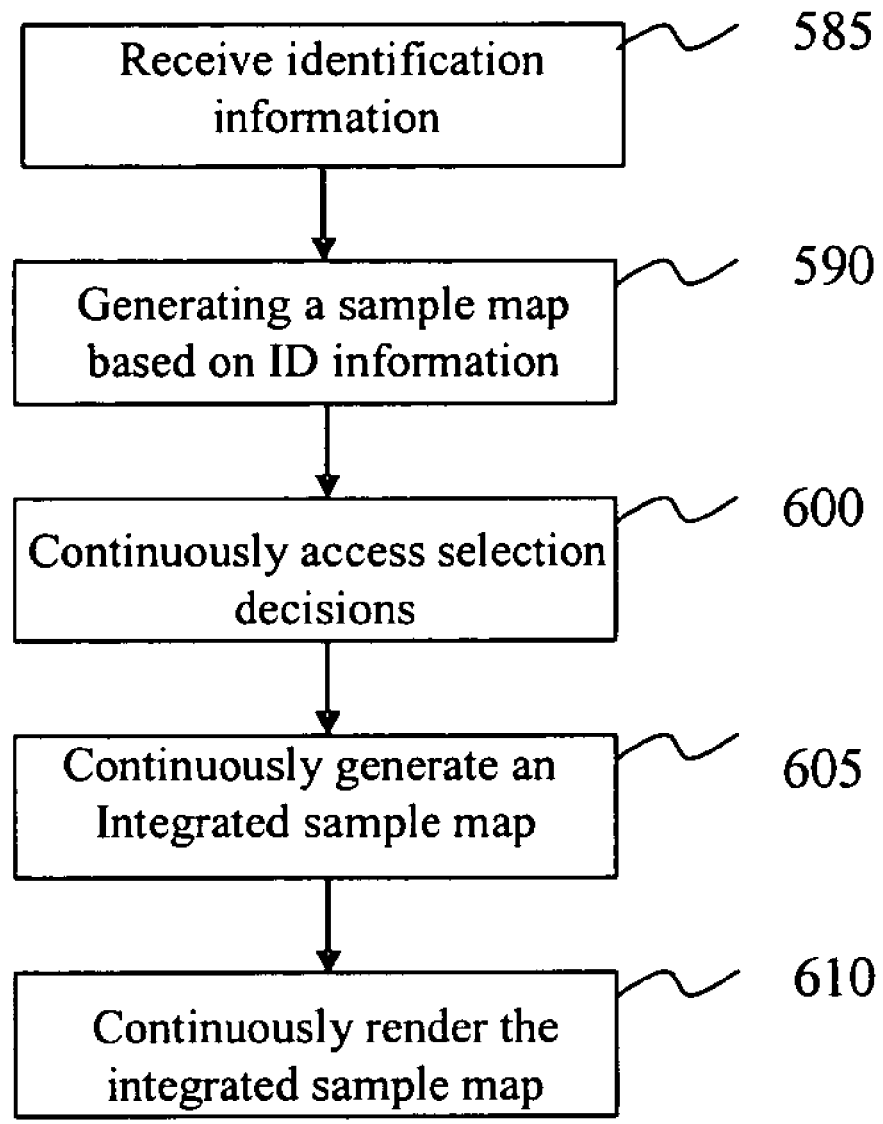
FIG. 6(b) is a simplified block diagram of the method embodiment shown in FIG. 6(a).

FIG. 6(a)–6(b) set forth flow diagrams for representative method embodiments of the present invention. In FIG. 6(a) a sample data base 550 is shown created with analytical information contained in a rack(s) and with the bar codes associated with those compounds. This data base is annotated with compound tube decision information (i.e., to cull) based on the analytical data, other information or chemist decision. After placing the multi-rack of tubes on the scanner reader, continuous readings of the sample ID step 560 is performed. Selections decisions are retrieved from a database, step 555, regarding which tubes should be selected, culled, or removed for further processing. There is then displayed the integrated dynamic selection map, step 565, which indicates operations to be taken with respect to the tubes in the array. As the operator actually performs the indicated operation, step 570, the display of the integrated dynamic selection map, step 565, is continuously updated to provide feedback (confirming to the operator that the correct operation was performed). This process of performing the indicated operations continues until the selection map is completed, step 575. A simplified version of such method is shown in FIG. 6(b). Identification information is received, step 585, from a tube reader and a sample map based on the ID information scanned generated, step 590. Such map is then altered to reflect information in the selection database, step 600, and an integrated sample map generated, step 605, which indicates not only the identify of each tube at a position in the array, but indicates the selection operations to be performed with respect one or more tubes in the array. The integrated sample map is displayed, step 610, such as on a video screen.

Figure 7:
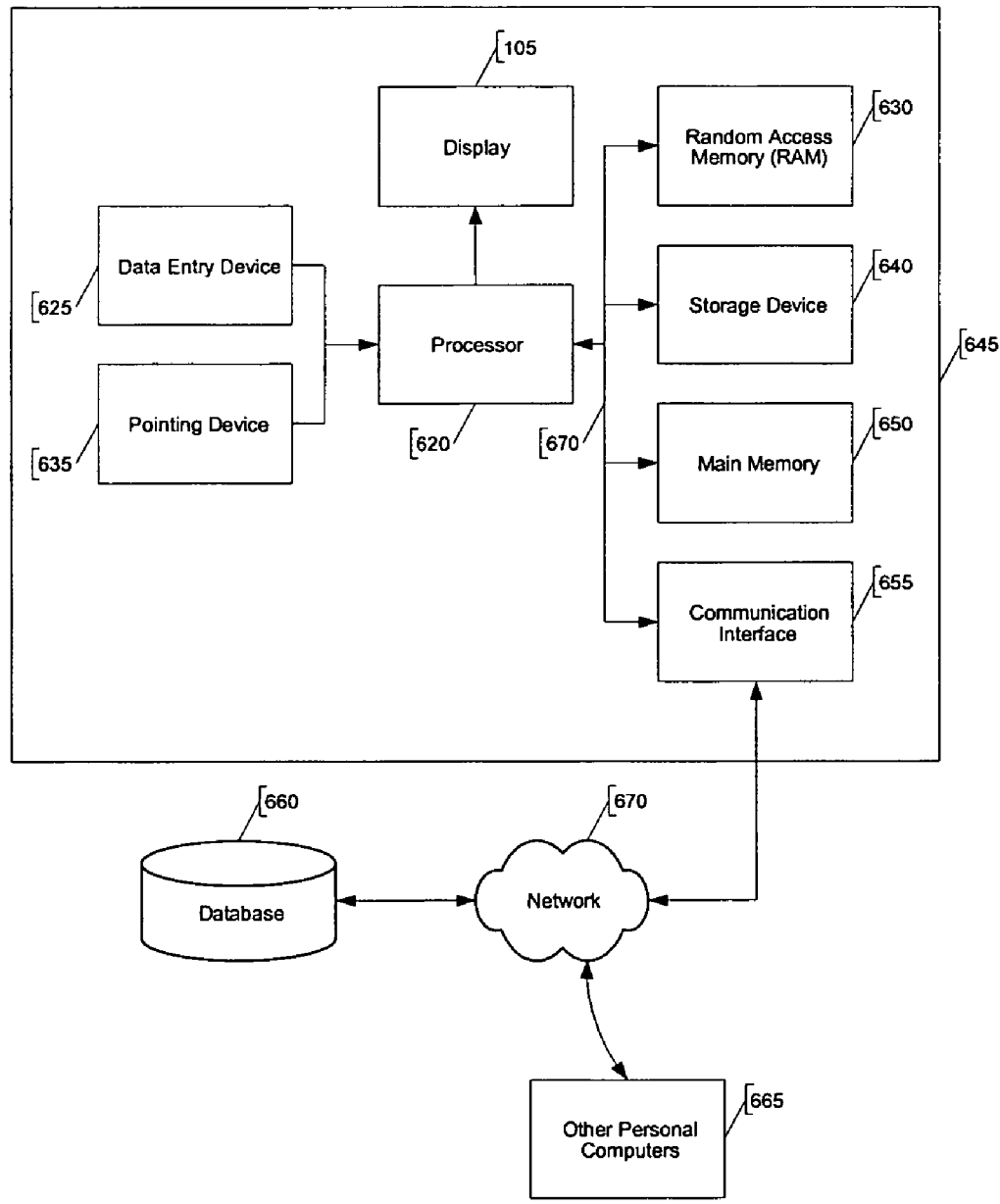
FIG. 7 is a diagrammatic representation of a conventional computing system useful in the present invention.

As would be understood by one of ordinary skill in the art, a computing system 645 useful in the present invention may be conventional, such as shown in FIG. 7. Advantageously such computing system 645 comprises processor 620, connected via bus 670, to Random Access Memory (RAM) 630, storage device 640 and main memory 650. It is advantageous that such computing system 645 be connected to data entry device 625, pointing device 635 and display 105. Such device may further have a communication interface 655 to allow communication with the database 660 or other commuters 665 in the network 670.

While the invention has been described with reference to the certain illustrated embodiments, the words that have been used herein are words of description, rather than words of limitation. Changes may be made, within the purview of the appended claims, without departing from the scope and spirit of the invention in its aspects. Although the invention has been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

What is claimed is:

1. A method comprising:
    (a) retrieving selection decisions associated with a plurality of samples stored in corresponding containers positioned in a structure in a certain configuration, wherein each sample is stored in a corresponding container and each selection decision is associated with a sample in a container indicating a certain operation to be performed on the corresponding container;
    (b) reading, continuously, identification information of the samples in the containers contained in the structure;
    (c) displaying a selection map display for samples in the containers of the structure, wherein the read identification information of each sample is shown at corresponding positions consistent with the configuration of the containers in the structure and a selection decision associated with the sample is integrally shown at the corresponding positions of the display;
    (d) performing an operation with respect to each sample according to a selection decision associated with the sample;
    (e) receiving updated identification information continuously read from the containers remaining in the structure; and (f) updating the selection map display according to the updated identification information and the selection decisions.

2. The method according to claim 1, wherein
the structure includes a rack; and
a sample stored in a corresponding container corresponds to a chemical compound.

3. The method according to claim 1, wherein the operation to be performed on a container in the structure includes:
   (a) picking a container if the selection decision associated with the sample in the container indicates such operation, or culling a sample if the selection decision associate with the sample in the tube is to cull the sample; and
   (b) reformatting the configuration of the containers in the structure to produce a different configuration of containers in the structure.

4. The method according to claim 1, wherein the identification associated with a sample is encoded in a two dimensional bar code.

5. The method according to claim 4, wherein the two dimensional bar code is substantially solvent resistant.

6. The method according to claim 1, wherein said displaying comprises:
   (a) receiving the continuously read identification information of the samples within containers in the structure, wherein the read identification information reflects the configuration of the containers;
   (b) generating a rack map of the containers held by the structure, wherein each container identified in the rack map is positioned correspondingly to the physical position where the container is located in the structure;
   (c) accessing a selection decision associated with each sample within a container in the structure;
   (d) generating an integrated sample map in which, for each sample within a container in the structure, the selection decision associated with the sample within a container is displayed with the identification of the sample in a container at a corresponding position consistent with the configuration of the samples; and
   (e) rendering the integrated sample map on a display device.

7. The method according to claim 1, further comprising making selection decisions prior to said retrieving selection decisions.

8. The method according to claim 7, wherein said making selection decisions comprises:
   (a) examining a sample in a container in a structure for which a selection decision is to be made based on at least one criterion;
   (b) making a selection decision with respect to each sample within a container in the structure based on the examination result from said examining; and
   (c) generating identification information associated with each sample wherein the identification information links the underlying container storing the sample to its associated selection decision.

9. The method according to claim 8, wherein the at least one criterion used in determining the selection decision with respect to a sample of a chemical compound in a container includes a condition expressed in terms of at least one of:
weight of the sample; or
purity of the chemical compound.

10. The method according to claim 8, further comprising entering an overriding selection decision by a human operator.

11. A system, comprising:
   (a) a structure configured to hold at least one container wherein each of the at least one container contain a corresponding sample and has identification information related to the sample;
   (b) a sample identification reader configured to continuously read the identification information on the containers of the samples contained in the structure; and
   (c) a dynamic sample configuration display mechanism configured to display the dynamic configuration of the containers contained in the structure based on the read identification information and selections decisions associated with the samples stored in the containers, wherein
   each of the selection decisions associated with a sample contained in the structure indicates an operation to be performed on the sample.

12. The system according to claim 11, wherein the identification information associated with a sample includes an identification to be used to identify the container storing the associated sample.

13. The system according to claim 12, wherein the identification associated with a sample is a two dimensional bar code.

14. The system according to claim 13, wherein the sample identification reader is an optical reader which decodes the two-dimensional bar codes.

15. The system according to claim 11, further comprising a selection decision database configured to provide storage, manipulation, and access for the selection decisions.

16. The system according to claim 15, wherein the selection decision database is implemented in a form including:
a file system;
a database management system; and
an Internet accessible data storage system.

17. The system according to claim 11, wherein the dynamic sample configuration display mechanism comprises:
   (a) a sample identification reading result receiver configured to receive the sample identification information of the samples contained in the structure read by the sample identification reader;
   (b) a selection decision retriever configured to retrieve the selection decisions associated with the samples contained in the structure based on the read sample identification information;
   (c) an integrated sample map generator configured to generate an integrated sample map based on the read sample identification information and the selection decisions of the samples contained in the structure; and
   (d) an integrated sample map display mechanism configured to render the integrated sample map on a display device.

* * * * *